(12) United States Patent
Horii et al.

(10) Patent No.: US 9,863,944 B2
(45) Date of Patent: Jan. 9, 2018

(54) IMMUNOCHROMATOGRAPHIC DIAGNOSIS KIT

(71) Applicant: ASAHI KASEI FIBERS CORPORATION, Osaka-shi, Osaka (JP)

(72) Inventors: Atsushi Horii, Tokyo (JP); Yoshiyuki Shiomi, Tokyo (JP); Takayuki Ogawa, Tokyo (JP); Takeshi Matsuse, Tokyo (JP); Maki Sugino, Tokyo (JP)

(73) Assignee: ASAHI KASEI FIBERS CORPORATION, Osaka (JP)

( * ) Notice: Subject to any disclaimer, the term of this patent is extended or adjusted under 35 U.S.C. 154(b) by 0 days.

(21) Appl. No.: 14/896,519

(22) PCT Filed: Jun. 9, 2014

(86) PCT No.: PCT/JP2014/065243
§ 371 (c)(1),
(2) Date: Dec. 7, 2015

(87) PCT Pub. No.: WO2014/199954
PCT Pub. Date: Dec. 18, 2014

(65) Prior Publication Data
US 2016/0123974 A1    May 5, 2016

(30) Foreign Application Priority Data

Jun. 10, 2013   (JP) .................. 2013-121898

(51) Int. Cl.
*G01N 33/53* (2006.01)
*G01N 33/543* (2006.01)
*G01N 33/558* (2006.01)

(52) U.S. Cl.
CPC ..... *G01N 33/54386* (2013.01); *G01N 33/558* (2013.01)

(58) Field of Classification Search
CPC .. G01N 33/53; G01N 33/585; G01N 33/5306; G01N 33/543; G01N 33/58
See application file for complete search history.

(56) References Cited

U.S. PATENT DOCUMENTS

| 5,266,497 A | 11/1993 | Imai et al. |
| 2010/0087552 A1 | 4/2010 | Shiomi et al. |

(Continued)

FOREIGN PATENT DOCUMENTS

| EP | 2 503 337 A1 | 9/2012 |
| EP | 2 781 918 | 9/2014 |

(Continued)

OTHER PUBLICATIONS

Office Action issued in European Application No. 14 810 4568.1 dated Jun. 22, 2016, 5 pages.

(Continued)

*Primary Examiner* — Jan Ludlow
(74) *Attorney, Agent, or Firm* — Finnegan, Henderson, Farabow, Garrett & Dunner, LLP (57) ABSTRACT

Provided is an immunochromatographic diagnostic kit which renders prompt diagnosis possible, has high analysis sensitivity, and gives test results with excellent reproducibility. The immunochromatographic diagnostic kit includes: a conjugate pad that contains a conjugate containing chromogenic particles which have an average particle diameter of 100-1,000 nm and attain a color intensity of 1.0-10.0, 10-90 wt % of the particles being derived from cellulose and 90-10 wt % of the particles being derived from a colorant; and a sample pad for an in vitro diagnostic reagent, the sample pad being constituted of nonwoven fabric that has a basis weight of 10-150 g/m² and a thickness of 0.07-1.00 mm and comprises regenerated cellulosic fibers.

5 Claims, 2 Drawing Sheets

(56) References Cited

U.S. PATENT DOCUMENTS

2012/0225496 A1    9/2012   Yoshida
2015/0079608 A1    3/2015   Tamura et al.

FOREIGN PATENT DOCUMENTS

| | | |
|---|---|---|
| JP | 61-128979 | 6/1986 |
| JP | 4-329965 | 11/1992 |
| JP | 7-55809 | 3/1995 |
| JP | 10-48215 | 2/1998 |
| JP | 11-170413 | 6/1999 |
| JP | 2955405 | 10/1999 |
| JP | 2012-108031 | 6/2012 |
| WO | WO 2006/080433 A1 | 8/2006 |
| WO | WO 2008/084854 A1 | 7/2008 |
| WO | WO 2011/062157 A1 | 5/2011 |
| WO | WO 2012/071145 A1 | 5/2012 |
| WO | WO 2013/071703 A1 | 5/2013 |
| WO | WO 2013/151066 A1 | 10/2013 |

OTHER PUBLICATIONS

Supplementary European search report from the European Patent Office for counterpart European Application No. EP 14 81 0458 dated May 27, 2016.

Written Opinion of the International Searching Authority dated Sep. 2, 2014 in International Application No. PCT/JP2014/065243.

English-language International Search Report from the Japanese Patent Office for International Application No. PCT/JP2014/065243 dated Sep. 2, 2014.

IMMUNOCHROMATOGRAPHIC DIAGNOSIS KIT

CROSS REFERENCE TO RELATED APPLICATIONS

This application is a national phase application based on PCT/JP2014/065243, filed Jun. 9, 2014, which claims the priority of Japanese Patent Application No. 2013-121898, filed Jun. 10, 2013, the contents of both of which are incorporated herein by reference.

TECHNICAL FIELD

The present invention relates to an immunochromatographic diagnostic kit containing a sample pad for an in vitro diagnostic reagent, and more specifically it relates to a lateral flow-type immunochromatographic diagnostic kit.

BACKGROUND ART

In recent years, convenient examination reagents, diagnostic reagents and diagnostic kits have been developed for conducting various examinations for the presence of pathogenic infection by viruses, bacteria or the like, the presence or absence of pregnancy, the presence or absence of cancer markers, and the presence or absence of specific raw materials or hazardous substances such as residual pesticides in foods, in short periods of time. These utilize specific reactions between the different substances to be examined and substances that specifically react with the substances to be examined. In particular, a large number of assay methods have been developed as immunoassays using antigen-antibody reaction between antigens and antibodies, including immunochromatographic assays, turbidimetric immunoassays, enzyme immunoassays, chemiluminescent assays, radioimmunoassays, assay methods using surface plasmon resonance, and the like. These assay methods are also utilized for disease examination at hospitals, clinics and the like, and for food examination at food companies, for example. Among these, immunochromatographic assays do not require special equipment, devices or knowledge and their operation is convenient and economical, while they also allow rapid diagnosis, and therefore they are commonly implemented in a large range of examinations. Pregnancy examination agents, HIV examination agents and the like have come to be sold at ordinary pharmacies in recent years, allowing measurement by ordinary consumers, and it has also become possible to perform not only qualitative examinations for examining the presence or absence of substances to be examined, but also quantitative examinations for measurement of their amounts.

The principle of measurement in an immunochromatographic assay may be that of the "sandwich method" or of the "competitive method". Moreover, the measurement system may be based on a flow-through method or a lateral flow method. It is possible to detect a variety of different substances as substances to be examined in a specimen, and a typical example is measurement by detection of antigen by the sandwich method, in which the following procedure is carried out in order.

(1) A antibody that specifically binds with an antigen as the substance to be examined is immobilized at a prescribed section of a chromatographic medium such as a nitrocellulose membrane, and a reaction site known as the "test line" (hereunder referred to as "TL") is formed at a desired location in the chromatographic medium.

(2) A detection reagent is prepared by supporting an antibody that specifically binds with the substance to be examined, on a labeling substance such as an enzyme, chromogenic particles, fluorescent particles, magnetic particles or the like, and the detection reagent is coated and dried onto a conjugate pad or the like, a detection reagent-containing section is formed, and this is combined with the chromatographic medium to form an immunochromatographic diagnostic kit.

(3) The actual specimen containing the antigen, or a solution containing it diluted with a desired liquid, is dropped onto a prescribed location of the immunochromatographic diagnostic kit, such as onto the sample pad, and the antigen and the detection reagent are developed on the chromatographic medium.

Using this series of procedures, the labeling substance is captured via the antigen on the antibody immobilized on the chromatographic medium at the reaction site, and the labeling substance signal is detected for diagnosis by the immunochromatographic diagnostic kit. Ordinarily, diagnosis is qualitative diagnosis that detects only the presence or absence of the antigen, but in recent years the strength of the signal can be visually or mechanically detected for quantitative diagnosis.

A rapid diagnosis time is a requirement for an immunochromatographic assay. This is in order to shorten the waiting time for the examination. A common method for meeting this requirement is a method of adjusting the pore sizes of the chromatographic medium to increase the traveling speed of the specimen.

Also, PTL 1 reports that a more rapid diagnosis time is possible by using a specific cellulosic fiber nonwoven fabric as the sample pad, at the section where the specimen sample containing the substance to be examined is to be dropped. PTL 1 mentions the liquid absorption speed and developability, but contains no concrete data for the diagnosis time and nowhere mentions a combination with specific chromogenic particles, as according to the present invention. In addition, it does not mention modification to the placement of the sample pad and conjugate pad.

Furthermore, PTL 2 reports that it is possible to achieve a more rapid diagnosis time by modifying the structure of the diagnostic kit and the like, but the shortest assessment in a hCG assay, for example, is 2 minutes and 35 seconds.

Increased analysis sensitivity is another requirement for an immunochromatographic assay. This means the ability to accomplish detection with an even lower amount of substance to be examined. In PTL 3, the present inventors have reported that analysis sensitivity can be increased by using cellulose particles having dense color and large particle diameters as the chromogenic particles. However, while it is mentioned that rapid diagnosis is possible by using chromogenic particles having dense color and large particle diameters, there is no concrete data for the diagnosis time and nothing is mentioned regarding combination with a specific sample pad, as according to the present invention.

Thus, there is generally a trade-off between speed of diagnosis time and increased analysis sensitivity, and a very great need exists for simultaneously achieving both.

In addition, PTL 4 discloses a semiquantitative test method using immunochromatography, and states that the antigen concentration and examination result signal strength can be made proportional for antigen concentrations in certain ranges. However, for quantitation in immunochromatography it is ideal to not only have proportionality between antigen concentration and examination result signal strength at certain antigen concentrations, but also to have reproducibility of test results, i.e. to obtain a signal of the same intensity when measuring antigen of the same concentration, but it is the general consensus that such reproducibility is still inadequate.

Also, PTL 5 discloses an immunochromatographic diagnostic kit using fluorescent particles as chromogenic particles, mentioning cellulose particles as an example for the material for the chromogenic particles and a cellulose nonwoven fabric as an example of the material for the sample pad, but neither are described in specific detail. In addition, it does not mention modification to the placement of the sample pad and conjugate pad. Naturally, nothing is mentioned regarding an effect by combination of the sample pad and the chromogenic particles, as according to the present invention.

CITATION LIST

Patent Literature

[PTL 1] Japanese Unexamined Patent Publication No. 2012-108031
[PTL 2] Japanese Unexamined Patent Publication HEI No. 7-55809
[PTL 3] International Patent Publication No. WO2011/062157
[PTL 4] International Patent Publication No. WO2006/080438
[PTL 5] International Patent Publication No. WO2013/151066

DISCLOSURE Of THE INVENTION

Problems to be Solved by the Invention

In light of the aforementioned prior art, the problem to be solved by the present invention is to provide an immunochromatographic diagnostic kit that allows more rapid diagnosis, has high analysis sensitivity and also has excellent reproducibility of examination results.

Means for Solving the Problems

The present inventors have conducted diligent research and much experimentation with the aim of solving this problem, and as a result have completed this invention upon finding, unexpectedly and surprisingly, that if particles with dense color and a large particle diameter are used as the chromogenic particles and a nonwoven fabric made of specific regenerated cellulosic fibers is used as the sample pad, by using these in combination, it is possible to increase the diagnosis speed and analysis sensitivity and to also achieve excellent reproducibility of examination results.

Specifically, the present invention is as follows.

[1] An immunochromatographic diagnostic kit including a conjugate pad containing a conjugate that includes chromogenic particles with an average particle diameter of 100 to 1000 nm and a color intensity of 1.0 to 10.0, the particle weight being 10 to 90 wt % derived from cellulose and 90 to 10 wt % derived from a colorant, and a sample pad for an in vitro diagnostic reagent composed of a nonwoven fabric made of regenerated cellulosic fibers, with a basis weight of 10 to 150 g/m$^2$ and a thickness of 0.07 to 1.00 mm.

[2] An immunochromatographic diagnostic kit according to [1] above, wherein the regenerated cellulosic fibers are composed mainly of cuprammonium rayon fibers.

[3] An immunochromatographic diagnostic kit according to [1] or [2] above, wherein the regenerated cellulosic fibers are continuous filaments.

[4] An immunochromatographic diagnostic kit according to any one of [1] to [3] above, wherein the fiber loss number of the nonwoven fabric composed of the regenerated cellulosic fibers is less than 5000/m$^2$.

[5] An immunochromatographic diagnostic kit according to any one of [1] to [4] above, wherein the colorant is a reactive dye.

[6] An immunochromatographic diagnostic kit according to any one of claims 1 to 5, wherein the coverage factor on the sample pad for the in vitro diagnostic reagent is 50 to 100% with respect to the conjugate pad.

Effect of the Invention

The immunochromatographic diagnostic kit of the invention includes prescribed chromogenic particles as the labeling substance, and employs a nonwoven fabric made of prescribed regenerated cellulosic fibers as the sample pad, whereby diagnosis is more rapid and the analysis sensitivity is increased, while the reproducibility of examination results is also excellent.

The present invention is an invention based on the finding by the present inventors that by combining prescribed chromogenic particles and a prescribed sample pad, it is possible to unexpectedly and surprisingly achieve a more rapid diagnosis time, increase the analysis sensitivity and increase the reproducibility of examination. As disclosed in PTL 3, it has been shown that chromogenic particles with a large particle diameter and high color intensity have higher analysis sensitivity even when used alone. In addition, such high analysis sensitivity also allows the diagnosis time to be shortened to some extent. However, because an immunochromatographic diagnostic kit comprises different porous structures such as the chromatographic medium, chromogenic particles with large particle diameters sometimes encounter interference with the pores of the porous structures, inhibiting their flow. When particles have been generated that have reduced flow, the diagnosis time can potentially be delayed. The present inventors considered that it may be possible to further shorten the diagnosis time by allowing chromogenic particles with large particle diameters to flow more easily. Upon repeated research based on this hypothesis, it was found that by using a nonwoven fabric made of regenerated cellulosic fibers and having low bulk density and a small thickness as the sample pad, it is possible to increase the flow rate per unit time for supply to the conjugate pad including the chromogenic particles, and to facilitate flow of the chromogenic particles in the conjugate pad, thereby shortening the diagnosis time. Chemical agents such as surfactants are sometimes added to facilitate the flow of chromogenic particles in sample pads, and since the sample pad of the present invention instantly absorbs a dropped specimen, it allows a fixed concentration of chemical agent to be constantly provided to facilitate flow of the chromogenic particles in the conjugate pad or chromatographic medium. Thus, the chromogenic particles easily flow without encountering interference in the pores of the porous structures. In an ordinary sample pad, the concentration of chemical agents that serve to facilitate flow of the chromogenic particles is not constant and clogging of the particles and the like can occur, but with the aforementioned effects it is possible to successfully allow all of the chromogenic particles to contribute to the examination, resulting in increased analysis sensitivity and also increased reproducibility of examination, while it was also found that it is possible to augment these effects by further modifying the placement of the sample pad and the conjugate pad.

BEST MODE FOR CARRYING OUT THE INVENTION

Embodiments of the invention will now be explained in detail.

The term "chromogenic particles", for the purpose of the invention, refers to particulate matter that is insoluble in water, buffering solutions and the like, and supports a pigment, dye or the like. The material composing the particles is not particularly restricted, and examples of such chromogenic particles include metal colloid particles such as gold colloid, platinum colloid, silver colloid, selenium colloid and the like, colored latex particles including colored styrene-based latexes such as polystyrene latex, or acrylic acid-based latexes, colored silica particles which are colored silica with a 3-dimensional structure made of silicon atoms and oxygen atoms, colored cellulose particles which are colored cellulose, and chromogenic particles or magnetic particles that are direct particles of a colorant such as carbon black. The chromogenic particles may also be fluorescent particles. Colored cellulose particles are preferred from the viewpoint of ease of adjustment of the particle characteristics, such as adjustment of the particle diameter, adjustment of the color intensity, adjustment of the color type, and adjustment of the particle surface condition. Because cellulose contains numerous hydroxyl groups, it has high hydrophilicity and excellent dispersion stability, and can contain large amounts of colorant.

There are no particular restrictions on the "method for producing the chromogenic particles". There may be mentioned a method in which the particles are first formed and then the colorant such as the pigment or dye is supported on them, a method in which particles are formed, and smaller chromogenic particles of a metal colloid or pigment are supported on them, or a method in which a colorant such as a coloring substance, dye, pigment, metal colloid or the like is added and formed together with formation of the particles. Preferred among these is a method in which particles are formed first and a colorant such as a pigment or dye is supported on them, from the viewpoint of ease of adjustment of the particle characteristics, including adjustment of the particle diameter, adjustment of the color intensity, adjustment of the color type and adjustment of the particle surface condition. A dye is preferred as the supported colorant, from the viewpoint of easier supporting.

When a dye is used as the colorant, the "type of dye" is not particularly restricted. There may be used dyes such as reactive dyes, direct dyes, auriferous dyes, acidic dyes, basic dyes, disperse dyes, sulfurized dyes, plant dyes, naphthol dyes, fluorescent dyes or the like. Any desired dyes may of course be used in combination. When cellulose is used as the particles, a reactive dye that binds to the hydroxyl groups of the cellulose by covalent bonding is most preferred from the viewpoint of allowing a large amount of dye to be held and from the viewpoint of stability.

When the cellulose particles are formed first and the colorant is supported afterwards, the "method of forming the cellulose particles" is not particularly restricted. There may be mentioned a method in which natural cellulose is physically micronized using a ball mill or a high-pressure homogenizer, a method in which it is chemically treated with an acid or alkali for micronization, or a method in which cellulose is dissolved in a good solvent and particles are formed. Alternatively, derivatized cellulose may be dissolved and particulates formed, and the derivatized substituents reconverted to hydroxyl groups to prepare cellulose particles. These forming methods may also be combined. The "type of cellulose" is also not particularly restricted, and there may be used regenerated cellulose, refined cellulose, natural cellulose, the aforementioned derivatized cellulose, or cellulose having derivatized substituents reconverted to hydroxyl groups. The preferred method among these is a method of dissolution in a good solvent and forming particulates, from the viewpoint of adjustment of the particle diameter, adjustment of the particle shapes, etc., while the preferred type of cellulose is regenerated cellulose.

When the cellulose is dissolved in a good solvent and particulates are formed, the "type of good solvent that dissolves cellulose" is not particularly restricted, and there may be used various good solvents that can dissolve cellulose, such as copper ammonia solution, viscose solution, N-methylmorpholine, and different ionic liquids and the like. Copper ammonia solution is preferred from the viewpoint of adjustment of the particle diameter, adjustment of the particle shapes, and the like. The method of forming the dissolved cellulose into particles is also not particularly restricted. A phase separation method was selected for the present invention.

The "average particle diameter" of the chromogenic particles is the volume-average median diameter as measured by the dynamic light scattering method, the volume-average median diameter being in the range of 100 to 1000 nm. If the average particle diameter is within this range, the particle surface area will be large, such that the TL will be darker, i.e. the analysis sensitivity will be higher, for use as an immunochromatographic diagnostic kit. If the average particle diameter is too small the surface area will be reduced and the analysis sensitivity may fall, or particle aggregation may occur. From this standpoint, the particle diameter is preferably 200 nm or greater and more preferably 300 nm or greater. If the particle diameter is too large, clogging of the pores of the chromatographic medium such as nitrocellulose will cause coloration of the sections that would otherwise be white after the examination, producing an adverse effect on judgment of the examination results and often impairing the detection limit. From this standpoint, the particle diameter is preferably no greater than 800 nm and more preferably no greater than 600 nm. The average particle diameter referred to here is only an average value, and a portion of the particle size distribution may be outside of the range.

The reason for using the volume-average for evaluation of the particle diameter is that very large particles in the immunochromatographic diagnostic kit clog the chromatographic medium, such as nitrocellulose, but larger particles have a greater effect based on volume-average, and therefore the effect of even a trace presence of large particles will be reflected. Other various methods of expression exist for evaluating the particle diameter in addition to volume-average, such as number-average and area-average. Naturally, a different method of expression will give a different particle diameter value, but volume-average is employed for the present invention.

The term "color intensity" is the value defining the color intensity of particles. As the method for measuring this value, a purified water dispersion of chromogenic particles with known concentration is prepared and subjected to visible spectrophotometry using an integrating sphere in a range of 400 to 800 nm with an optical path length of 10 mm, the peak value of the obtained absorbance curve (ABS) is measured, the obtained value is divided by the weight percent of the chromogenic particles, and the result is defined as the value in terms of absorbance per 0.01 wt % of chromogenic particles. For example, if the concentration of the prepared chromogenic particles is 0.0045% and the peak value of the absorbance curve is 1.0, the color intensity is $(1 \times 0.01) \div 0.0045 = 2.2$.

The reason for conducting visible spectrophotometry using an integrating sphere for measurement of the color intensity of the particles is to allow the most accurate measurement of the color intensity of the particles in a state dispersed in liquid. Another method for measuring the color intensity of the particles is a method of measurement of a solid obtained by drying the particles, using a colorimeter or the like, but accurate measurement of the color intensity of the particles is not possible by such a method. For example, metal colloids and the like differ in their color tone and maximum wavelength depending on the particle diameter, and the dried aggregated state cannot accurately reflect the color intensity exhibited in a liquid-dispersed state. Furthermore, the color intensity is reduced when aggregation occurs in a liquid, even if dispersion is at the same particle concentration. In addition, the reason for using an integrating sphere for the visible spectrophotometry is in order to eliminate the effect of scattering of the particles themselves. Ordinary visible spectrophotometry is a method of measuring transmitted light, and it will reflect not only absorption of an incident beam by the colorant but also the influence of scattering of the particles themselves. For example, gold colloids commonly used for immunochromatography have particle diameters of 40 nm to 60 nm, and sometimes up to even 100 nm, and since these are all small particle diameters, there is virtually no effect on scattered light. In contrast, polystyrene latex particles have large particle diameters and clearly the effect on scattered light is considerable. For this reason, in order to more accurately reflect the color intensity of the particles themselves when particle diameters or particle materials differ, the present invention employs visible spectrophotometry using an integrating sphere.

The "color intensity" according to the invention is 1.0 to 10.0. If the value is too large, the color intensity becomes darker and the analysis sensitivity increases when used as an immunochromatographic diagnostic kit. A larger value is better of course, and there may be employed a method such as utilizing a dark-colored dye, increasing the number of dyeings, linking through some compound used as a spacer, increasing the amorphous regions of the particles to facilitate infiltration of the dye, or creating porosity in the particles to facilitate infiltration of the dye. In consideration of economy, however, the upper limit is preferably no greater than 7.0 and more preferably no greater than 5.0. Also, since a smaller value lowers the analysis sensitivity for use as an immunochromatographic diagnostic kit, the lower limit is preferably 1.5 or greater and more preferably 2.0 or greater.

The "proportion of the colorant in the chromogenic particles" is the proportion of colorant of the total weight of the chromogenic particles. For example, when 1.0 g of chromogenic particles consists of 0.2 g of cellulose and 0.8 g of colorant, the proportion of colorant is 80 wt %. The proportion of the colorant in the chromogenic particles is preferably 10 to 90 wt %. Within this range, the analysis sensitivity will be high for use as an immunochromatographic diagnostic kit. Also, when dyed particles that are dyed cellulose are used as the chromogenic particles, having the dye held in this range in the cellulose allows a suitable degree of hydrophobicity to be imparted to the cellulose, and allows substances that specifically bind with detection targets such as antibodies to be held by adsorption. Naturally, rather than holding by adsorption, it is possible to introduce carboxyl groups or amino groups into the colored cellulose particles to allow holding of substances that specifically bind to detection targets by covalent bonding. If the proportion of the colorant is low it will not be possible to obtain sufficient color intensity, and the analysis sensitivity will be reduced when used as an immunochromatographic diagnostic kit. Furthermore, when particles that are cellulose and dyed with a dye are used as the chromogenic particles, it is sometimes possible to even increase substances that specifically bind with the detection target by increasing the proportion of colorant. From this viewpoint, the lower limit is preferably 20 wt % or greater and more preferably 30 wt % or greater. While there is no particular problem even if the proportion of colorant exceeds 90 wt %, it is preferably no greater than 85 wt % and more preferably no greater than 80 wt %, when economic considerations are taken into account. Also, if the hydrophobicity is too strong, aggregation or nonspecific reactions may occur.

The "method of calculating the proportion of the colorant in the chromogenic particles" may be calculation from the weight change before and after coloration. When calculation from the weight change is difficult, a procedure of separating the colorant from the particles may be carried out and the colorant or particles isolated to perform the calculation. For example, when the cellulose particles have been dyed with a reactive dye, the covalent bonds between the cellulose and the dye may be broken with an acid or alkali, and the cellulose particles collected by centrifugal separation for calculation. Also, cellulase may be used for decomposition of the cellulose alone, and calculation performed.

The "method of calculating the cellulose-derived component of the chromogenic particles" may be calculation from the aforementioned proportion of the colorant in the chromogenic particles, specifically, the calculation may be performed by the formula: "Proportion of cellulose-derived component of the chromogenic particles"=100%−(proportion of the colorant in the chromogenic particles). The proportion of the cellulose-derived component of the chromogenic particles is preferably 90 to 10 wt %. Within this range it will be possible to maintain dispersion stability for the cellulose particles. Also, for the same reason mentioned for the proportion of the colorant, the lower limit for the cellulose-derived component of the chromogenic particles is more preferably 15 wt % or greater and most preferably 20 wt % or greater, and the upper limit is more preferably no greater than 80 wt % and most preferably no greater than 70 wt %.

The term "particles" refers to structures having similar lengths for the long diameter (L) and the short diameter (D), and having nearly spherical shapes. Specifically, it refers to structures having an L/D ratio represented by L÷D of 1.0 to 3.0. If the L/D ratio is within this range, clogging will be inhibited when used as an immunochromatographic diagnostic kit, the ratio being more preferably 1.0 to 2.0, even more preferably 1.0 to 1.5 and most preferably 1.0 to 1.3. As the measuring method, an electron microscope image of the particles is taken, the long diameters (L) and short diameters (D) of 100 particles are measured, and the average value for the 100 particles is calculated.

The term "regenerated cellulosic fibers" refers to fibers composed mainly of regenerated cellulose. The regenerated cellulose may be cupra, lyocell, rayon or the like. Regenerated cellulosic fibers have very high hydrophilicity due to the orientation and state of the surface molecules during formation of the fibers, as well as excellent liquid absorption properties, and are therefore preferred as the material for composing the sample pad, with cupra and lyocell being more preferred and cupra being most preferred. It may be composed of 100% of specific regenerated cellulosic fibers, or they may be used in admixture.

The phrase "nonwoven fabric made of regenerated cellulosic fibers" refers to a nonwoven fabric made of the aforementioned regenerated cellulosic fibers. The structure can be easily formed with a nonwoven fabric, and handling is also excellent, allowing winding into a roll or the like. The type of nonwoven fabric may be a staple fiber nonwoven fabric or long filament nonwoven fabric, but a continuous filament nonwoven fabric is preferred for its excellent water absorbing properties and low fiber loss. Also, for control of the form stability and liquid absorption speed, synthetic fibers may be mixed therewith in a range that does not impair the hydrophilicity, in which case the content of the regenerated cellulosic fibers is preferably at least 50 wt % of the area ratio. Synthetic fibers are not particularly restricted so long as they satisfy the desired physical properties of the sample pad, and may be, for example, polyolefin-based, polyester-based, polyamide-based or acrylic-based synthetic fibers, any one or more of which may be used. These may also be used with a binder if necessary, or subjected to tangling treatment or the like.

The "basis weight of the nonwoven fabric made of regenerated cellulosic fibers" is 10 to 150 g/m$^2$. The basis weight may vary appropriately depending on the size of the sample pad, the liquid volume of the specimen, the type of examination, etc., but if the basis weight is within the aforementioned range, a satisfactory balance will be obtained for absorption of specimen fluid and development on the conjugate pad, and after the specimen has been rapidly absorbed it will be possible to rapidly supply the specimen to the conjugate pad. A nonwoven fabric with an excessively low basis weight will have a small thickness or a high void percentage, and poor migration of specimen fluid into the sample pad and developability on the conjugate pad. From this viewpoint, the lower limit for the basis weight is preferably 15 g/m$^2$ or greater, more preferably 20 g/m$^2$ or greater and most preferably 25 g/m$^2$ or greater. Also, a nonwoven fabric with an excessively high basis weight will have a large thickness or low void percentage, and specimen fluid will not be able to easily penetrate into the sample pad, causing the fluid to slide over the sample pad. From this viewpoint, the upper limit for the basis weight is preferably no greater than 120 g/m$^2$ and more preferably no greater than 100 g/m$^2$.

The "thickness of the nonwoven fabric made of regenerated cellulosic fibers" is 0.07 to 1.00 mm. The thickness may vary appropriately depending on the size of the sample pad, the liquid volume of the specimen, the type of examination, etc., but if the thickness is within the aforementioned range, a satisfactory balance will be obtained for absorption of specimen fluid and development on the conjugate pad, and after the specimen has been rapidly absorbed it will be possible to rapidly supply the specimen to the conjugate pad. If the thickness is too small, it will not be possible to adequately receive specimen fluid. Handling of the diagnostic kit will also become more difficult during the production steps. From this viewpoint, the lower limit for the thickness is preferably 0.10 mm and more preferably 0.20 mm. Also, if the thickness is too large, too much specimen fluid will be held, which is undesirable. From this viewpoint, the upper limit for the thickness is preferably no greater than 0.80 mm and more preferably no greater than 0.70 mm.

The bulk density of the nonwoven fabric made of regenerated cellulosic fibers" is preferably 0.06 to 1.00 g/cm$^3$. The bulk density may vary appropriately depending on the size of the sample pad, the liquid volume of the specimen, the type of examination, etc., but if the bulk density is within the aforementioned range, a satisfactory balance will be obtained for absorption of specimen fluid and development on the conjugate pad, and after the specimen has been rapidly absorbed it will be possible to rapidly supply the specimen to the conjugate pad. If the bulk density is too low, the voids in the fibers will increase, leading to poor migration of specimen fluid into the sample pad and developability on the conjugate pad. From this viewpoint, the lower limit for the bulk density is preferably 0.07 g/cm$^3$ and more preferably 0.10 g/cm$^3$. Also, if the bulk density is too high, the fibers will become too compact and specimen fluid will not be able to easily penetrate into the sample pad, causing the fluid to slide over the sample pad. From this viewpoint, the upper limit for the bulk density is preferably no greater than 0.70 g/cm$^3$ and more preferably no greater than 0.50 g/cm$^3$.

The "fiber loss number" is the number of fibers with sizes of 100 μm or greater that are lost per unit square meter when a 25 cm×25 cm sample is placed in 300 ml of purified water and allowed to stand for 2 minutes, and then the sample is removed and the remaining fluid is filtered with black filter paper (ADVANTEC NO131), the filter paper after filtration is set in a thermostatic chamber (20° C., 65% RH) for 12 hours and dried and the count is determined using a video microscope. According to the invention, the fiber loss number is preferably less than 5000/m$^2$, more preferably less than 4000/m$^2$, and even more preferably less than 3000/m$^2$. If the fiber loss number is greater than 10,000/m$^2$ this is undesirable because the fibers will easily drop off, and depending on the type of examination fluid, the fallen fibers will accumulate at the interface between the sample pad and the conjugate pad, impairing the developability and also contaminating the area around the production line during production, tending to result in poor yield. Since a lower fiber loss number is preferred, the lower limit is as low as 1/m$^2$.

Figure 1:
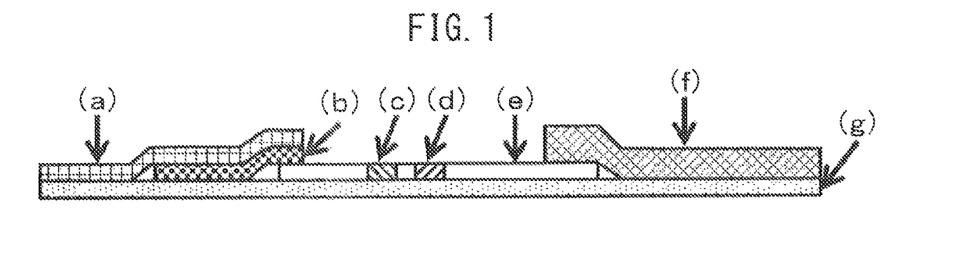
FIG. 1 is a cross-sectional view of an immunochromatographic diagnostic kit as one embodiment of the invention.

As shown in FIG. 1(a), the "sample pad" according to the invention is the section that first receives a specimen that is to be measured by immunochromatography. Common sample pads include cellulose filter paper, paper, glass fibers, glass fibers, acrylic fibers nylon fibers and various woven fabrics, but for the invention the sample pad used is a nonwoven fabric made of regenerated cellulosic fibers, as mentioned above. The nonwoven fabric made of regenerated cellulosic fibers has excellent liquid absorption properties, and therefore the specimen is rapidly absorbed and the specimen can migrate into the conjugate pad. Furthermore, if the structure of the nonwoven fabric made of regenerated cellulosic fibers is the structure described above, it is possible to increase the flow rate per unit time for supply to the conjugate pad, and to better facilitate initial release of the chromogenic particles in the conjugate pad, thereby shortening the diagnosis time. Also, a chemical agent for facilitating flow of the chromogenic particles can be supplied at a constant fixed concentration, to allow easier flow without clogging of the chromogenic particles. Since, as a result of this, almost all of the particles can contribute to the examination, the analysis sensitivity is increased and the reproducibility of examination can also be improved. Conversely, when the chromogenic particles in the conjugate pad are not initially released, the diagnosis time is lengthened. Moreover, when virtually all of the chromogenic particles are not released from the conjugate pad, the analysis sensitivity is reduced and the reproducibility of examination is poor.

According to the invention, the nonwoven fabric made of regenerated cellulosic fibers may contain different chemical agents or powders, or a portion of the cellulose may be derivatized, for control of the hydrophilicity/water-repellency of the sample pad or the water absorption factor, so long as the aforementioned physical properties are not adversely affected and the antigen-antibody reaction and antibody stability are not affected. Examples of chemical agents to be impregnated include surfactants, proteins, antibodies, resins, water-soluble polymers, antimicrobial agents, antiseptic agents, antioxidants and the like. Also, examples of derivatized cellulose forms include carboxymethylated, carboxyethylated, primary aminated, secondary aminated, tertiary aminated, quaternary aminated and hydroxylated forms.

According to the invention, the sample pad may be subjected to pretreatment if necessary. For example, it may be subjected to treatment for pre-addition of a buffering solution, a surfactant, a protein, a reagent to trap contaminants in the specimen sample, an antiseptic agent, an antimicrobial agent, an antioxidant, a humectant or the like. Also, there is no particular restriction on the form of the sample pad, and for example, the size of the sample pad is such that the length (length flowed by the fluid) is preferably about 10 to 25 mm in consideration of the associating property from the specimen fluid, and the diagnosis time, while there is no problem if the width (perpendicular to the flow of the fluid) is larger than the width of the conjugate pad. If the width is too narrow, the examination fluid can potentially seep around the edges of the sample pad.

The "immunochromatographic diagnostic kit" of the present invention conveniently detects the presence or absence of a substance to be examined in various specimens. The type of diagnostic kit may be a lateral flow system or a flow-through system. It is not particularly restricted so long as it uses chromogenic particles and a sample pad, but it is preferably a lateral flow system. Lateral flow systems include dip stick types and cassette types, and there is no particular restriction on the type. The construction of the diagnostic kit is not particularly restricted, and may be any construction commonly employed in the field. The types of members other than the conjugate pad (b) containing the antibody-sensitized chromogenic particles and the sample pad (a) are not particularly restricted so long as they are ones that are employed in the field, and for example, there may be mentioned (e) a chromatographic medium, (f) an absorbent pad and (g) a mount board, as shown in FIG. 1. Some of these members may be omitted if necessary. An example for the structure is the structure shown in FIG. 1 of PTL 1. FIG. 1 accompanying the present specification is merely an example and places no limitations whatsoever on the present invention.

The "conjugate pad" is a pad containing a conjugate that includes chromogenic particles, and for example, it may contain chromogenic particles bound to an antibody that binds to the substance to be examined. There are no particular restrictions on the material of the conjugate pad, and common glass fibers, resin fibers or the like may be used. There may be suitably used resin fibers including resin fibers that are polyethylene or other polyolefin-based, or polyester-based, polyamide-based, acrylic or the like, as well as composite fibers of these resin fibers, with there being no limitation to these. Resin fibers are preferred from the viewpoint of the working environment. Among resin fibers, materials with a certain degree of hydrophobicity are more preferred from the viewpoint of easier release of the chromogenic particles. If the hydrophobicity is too high, pretreatment with a surfactant or the like may be used. More preferred is a polyethylene fiber conjugate pad that has been pretreated with a surfactant.

According to a preferred embodiment, the coverage factor of the sample pad on the conjugate pad is preferably 50 to 100%. The coverage factor referred to here is the proportion of coverage by the sample pad with respect to the top area of the conjugate pad. For example, the value is 0% when absolutely none of the sample pad overlaps with the top of the conjugate pad, and 100% when it completely covers it. For the calculation method, the area (A) at the section where the conjugate pad and the sample pad overlap and the area (B) of the entire conjugate pad are determined, and calculation is performed by the following formula.

$$\text{Coverage factor (\%)} = \text{area } (A) \text{ of overlapping section/total area } (B)/100$$

In a common immunochromatographic diagnostic kit, the coverage factor is usually no greater than 50%. For example, in PTL 1 the overlapping portion of the sample pad is 5 mm compared to 15 mm as the conjugate pad length, and therefore the coverage factor is 33%. In PTL 5 the coverage factor is 0%. In a common immunochromatographic diagnostic kit, the specimen supplied to the sample pad migrates to the conjugate pad, and then further migrates into the chromatographic medium. If the coverage factor is low at this time, the specimen will migrate into the chromatographic medium with the specimen failing to be sufficiently supplied to the downstream end of the conjugate pad at the section that is not in contact with the sample pad, and as a result, when the chromogenic particles have large particle diameters as according to the present invention, release from the conjugate pad may be slowed. Thus, according to the invention the coverage factor is 50% to 100% so that the specimen is rapidly supplied even to the downstream end of the conjugate pad, and release of the chromogenic particles can be more rapid. In order to improve the release property, the preferred lower limit for the coverage factor is 60%, more preferably 70%, even more preferably 80% and most preferably 90%.

Figure 2:
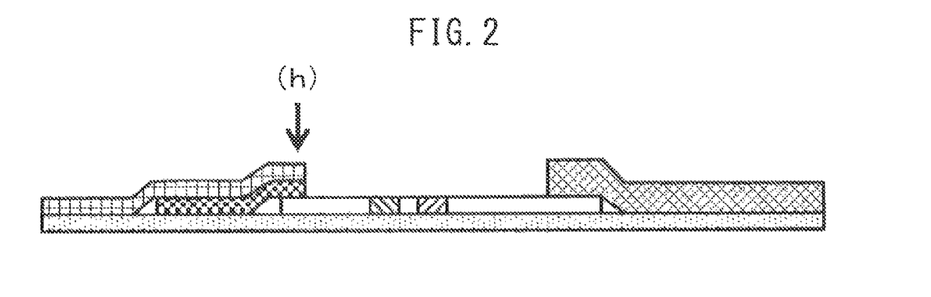
FIG. 2 is a cross-sectional view of an immunochromatographic diagnostic kit as an embodiment of the invention, showing the furthest downstream section (h) of the sample pad, where the coverage factor of the sample pad on the conjugate pad is 100%.
Figure 3:
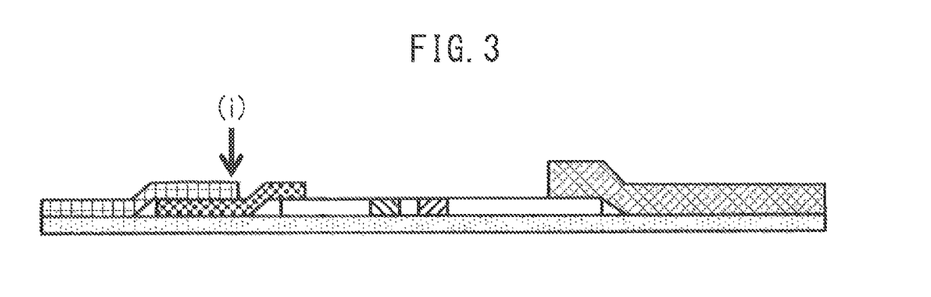
FIG. 3 is a cross-sectional view of an immunochromatographic diagnostic kit as an embodiment of the invention, showing the furthest downstream section (i) of the sample pad, where the coverage factor of the sample pad on the conjugate pad is 50%.
Figure 4:
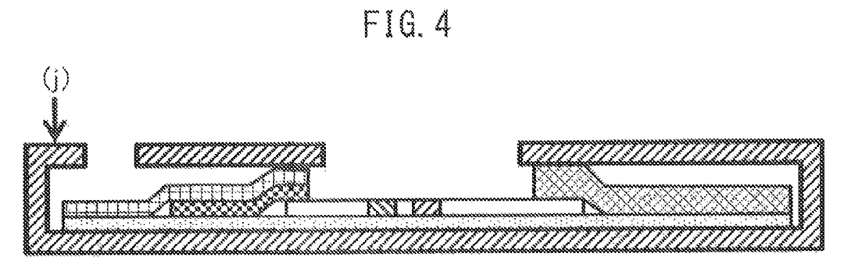
FIG. 4 is a cross-sectional view of an immunochromatographic diagnostic kit as an embodiment of the invention, with the coverage factor of the sample pad on the conjugate pad at 100%, and showing a state where it is set inside an enclosure (j).

On the other hand, when the coverage factor of the sample pad with respect to the conjugate pad has been increased as according to the present invention, the downstream end of the sample pad may rise off from the conjugate pad, depending on the construction of the immunochromatographic diagnostic kit. This occurs when the sample pad adhering to the mount board cannot follow the shape of the conjugate pad and curls upward. In order to solve this problem, a structure in which the furthest downstream section of the sample pad is reduced is preferred. The reducing method may be a method of placing the immunochromatography kit in an enclosure and reducing the portion at the enclosure section, or a method of using a transparent sheet provided with a bonding surface. The optimal degree of reduction will depend on the construction of the immunochromatographic diagnostic kit and therefore cannot be specified for all cases, but as a general range, for example, the furthest downstream section of the sample pad is preferably adjusted to be −5 to +2 mm with respect to the total thickness of the immunochromatographic diagnostic kit member. The furthest downstream section of the sample pad will have a different location depending on the coverage factor of the sample pad. For example, the furthest downstream section (h) in the case of a 100% coverage factor is shown in FIG. 2, and the furthest downstream section (i) in the case of a 50% coverage factor is shown in FIG. 3. FIG. 2 and FIG. 3 are merely examples and place no limitations whatsoever on the present invention. Also, the total thickness of the immunochromatographic diagnostic kit member, at the furthest downstream section of the sample pad in FIG. 2, for example, where the sample pad, the conjugate pad, the chromatographic medium and the mount board overlap, it is the sum of the thicknesses of these members. If the total thickness at the furthest downstream section of the sample pad exceeds +2 mm of the total thickness of the immunochromatographic diagnostic kit member, the sample pad may rise off from the conjugate pad and the colored cellulose particles in the conjugate pad may not be adequately released, and it is therefore preferably no greater than the total thickness +1 mm, and more preferably no greater than the total thickness +0 mm. On the other hand, if the total thickness of the furthest downstream section of the sample pad is less than −5 mm with respect to the total thickness of the immunochromatographic diagnostic kit member, the conjugate pad or chromatographic medium may become too compressed, potentially causing clogging during development of the chromogenic particles, and therefore it is preferably no less than −3 mm and more preferably no less than −1 mm with respect to the total thickness of the members. FIG. 4 shows adjustment of the thickness using an enclosure (j). An enclosure generally consists of an upper part and a lower part, and adjustment of their clearance allows the thickness to be adjusted. FIG. 4 is merely an example and places no limitations whatsoever on the present invention.

The "diagnostic method" using the immunochromatographic diagnostic kit of the invention refers to various manners of diagnosis conducted using immunochromatographic diagnostic kits. The target of diagnosis is not particularly restricted, and the kit may be used for examination of various diagnostic targets, including examination of humans, animals, food or plants, or environmental monitoring. In a common diagnosis procedure, a specimen sample is harvested from the target of examination, subjected to pretreatment such as extraction and filtration if necessary, and dropped onto the sample pad, a prescribed time is allowed to elapse from the start of the examination, and the diagnosis results are judged based on the color difference produced by the presence or absence of the substance to be examined. There is naturally no limitation to this procedure, and application may be made to diagnoses by similar procedures and principles. Preferably, the specimen sample is filtered beforehand to remove the excess foreign matter or contaminants, in order to allow more rapid diagnosis and to improve the diagnosis precision.

According to the invention, instead of a method of dropping the specimen directly onto the sample pad, there may be dropped a dilution of the specimen at a desired dilution factor in a treatment solution prepared with a prescribed composition. The purpose for using a specimen treatment solution may be addition of components that facilitate reaction of the antigen in the specimen, components that decompose contaminants in the specimen, components that trap contaminants in the specimen, components that reduce nonspecific reactions, components that facilitate flow of the chromogenic particles, components that cause suitable aggregation of the chromogenic particles to improve visibility when they are trapped in the test line, or the like. As examples, there may be added buffeting solutions, surfactants, proteins, inorganic salts, water-soluble polymers, reducing agents, chelating agents and the like. Particularly when using chromogenic particles according to the invention, it is possible to add a nonionic surfactant, various water-soluble amino acids, proteins, inorganic salts, water-soluble polymers, or the like. The specific types of components and their amounts will differ depending on the examination target and the type of antibody used, but examples of nonionic surfactants include poly(oxyethylene)alkyl ethers, poly(oxyethylene)octylphenyl ethers and poly(oxyethylene) nonylphenyl ethers. Examples of water-soluble amino acids include asparagine, aspartic acid, alanine, arginine, isoleucine, glycine, glutamine, glutamic acid, cysteine, serine, tyrosine, tryptophan, threonine, valine, histidine, proline, phenylalanine, methionine, lysine and leucine. Examples of proteins include casein, skim milk, casein digest, bovine serum albumin and fish gelatin. Preferred as inorganic salts are compounds that produce alkali metal ions such as sodium, potassium and lithium. Preferred water-soluble polymers are polyethylene glycol, polyvinyl alcohol, polyvinylpyrrolidone, carboxymethyl cellulose, and other cellulose derivatives. Also, these components may be not only added to the specimen treatment solution but also preadded to the sample pad, conjugate pad, chromatographic medium, (nitrocellulose membrane) or the like.

There are no particular restrictions on the subject that may be diagnosed with the immunochromatographic diagnostic kit of the invention, and as specific examples there may be mentioned the following: cancer markers, hormones, infectious diseases, autoimmunity, plasma proteins, TDM, coagulation/fibrinolysis, amino acids, peptides, proteins, genes and cells. More specifically, these include CEA, AFP, ferritin, β2-microglobulin, PSA, CA19-9, CA125, BFP, elastase-1, pepsinogen-1 and -2, fecal occult blood, urinary β2-microglobulin, PIVKA-2, urinary BTA, insulin, E3, HCG, HPL, LH, HCV antigen, HBs antigen, HBs antibody, HBc antibody, HBe antigen, HBe antibody, HTLV-1 antibody, HIV antibody, HIV antigen, HIV virus genes. Toxoplasma antibody, syphilis, ASO, Influenza A antigen, Influenza A antibody, Influenza B antigen, Influenza B antibody, rotavirus antigen, adenovirus antigen, rotavirus/adenovirus antigen, Group A *Streptococcus*, Gr B *Streptococcus, Candida* antigen, CD bacteria, *Cryptococctis* antigen, cholera bacteria, meningococcus antigen, granulocyte elastase, *Helicobacter pylori* antibody, O157 antibody, O157 antigen, *Leptospira* antibody, *Aspergillus* antigen, MRSA, RF, total IgE, LE test, CRP, IgG, A, M, IgD, transferrin, urinary albumin, urinary transferrin, myoglobin, C3/C4, SAA, LP(a), α1-AC, α1-M, haptoglobin, microtransferrin, APR score, FDP, D dimer, plasminogen, AT3, α2PI, PIC, PAI-1, protein C, clotting factor X3, typo IV collagen, hyaluronic acid and GRbA1c, as well as various other types of antigens, antibodies, viruses, bacteria, amino acids, peptides, proteins, DMA, cells, allergens, residual pesticides and toxins.

According to the invention, the chromogenic particles roust support a substance that specifically binds to the substance to be detected, such as an antibody, but there is no particular restriction on the method in which it is supported. For example, it may be supported by physical adsorption, by covalent bonding, or by a combination thereof. The type and amount of substance to be supported is not particularly restricted. The type of substance to be supported is most generally preferred to be an antibody. The supporting method is preferably supporting by physical adsorption from the viewpoint of ease, or supporting by covalent bonding from the viewpoint of stability and performance.

According to the invention, the chromatographic medium to be used in the immunochromatographic diagnostic kit is not particularly restricted, and various commonly used chromatographic media may be used. More specifically, it may be a nitrocellulose membrane. Commercially available nitrocellulose membranes are classified by the time necessary to move through a fixed distance, known as the flow rate, and membranes with faster flow rates have larger pore sizes. According to the invention, a membrane with a larger pore size is preferred because it has faster movement of specimen and also resistance to clogging by the chromogenic particles. Specifically, a membrane with a flow rate of faster than 120 sec/4 cm is preferred, a membrane with a flow rate of faster than 100 sec/4 cm is more preferred, and a membrane with a flow rate of faster than 90 sec/4 cm is even more preferred.

Examples for the method of preparing the cellulose particles, the method of coloring the cellulose particles, the method of preparing a regenerated cellulose continuous filament nonwoven fabric and the method of preparing the immunochromatographic diagnostic kit, will be described with the implicit understanding that the invention is in no way restricted by the descriptions.

[Method of Preparing Cellulose Particles]

Cellulose linter is dissolved in a good solvent for cellulose. For the present invention, a copper ammonia solution prepared by a known method was used as the good solvent. The solidifying solution used was mainly an organic solvent+water+ammonia mixture. The solidifying solution was stirred while adding a prepared copper ammonia-cellulose solution, for solidification. Also, by adding sulfuric acid for neutralization and regeneration, it is possible to obtain a slurry containing the desired cellulose particles. In such a case, the slurry will be acidic due to residue of the acid used for regeneration, and will also contain impurities such as ammonium salts generated by neutralization, and therefore a procedure is required for purification to a cellulose dispersion composed of the cellulose particles and the medium. The purification procedure used for the invention is repeated treatment with centrifugal separation-decantation-dispersing medium liquid dilution. Since the cellulose particles in the obtained cellulose particle dispersion will sometimes aggregate during the course of the purification procedure, dispersion treatment may be carried out by shearing or the like in such cases. The means used to apply shearing for the invention is a high-pressure homogenizer.

[Method of Coloring Cellulose Particles]

Sodium sulfate and a reactive dye are added to the obtained aqueous dispersion of cellulose particles, and the temperature is increased to a suitable temperature in a thermostatic bath, while stirring with a magnetic stirrer. After temperature increase, sodium carbonate is added as an alkali and dyeing is initiated. After a prescribed time has elapsed, it is possible to obtain a slurry containing the desired dyed cellulose particles. Because the slurry is alkaline at this time and includes sodium sulfate, unreacted dye and the like, it is necessary to carry out a procedure for purification to a dyed cellulose particle dispersion comprising the dyed cellulose particles and the medium. Purification is carried out by centrifugal separation in the same manner as above, to obtain a dyed cellulose particle dispersion. Since the cellulose particles in the obtained dyed cellulose particle dispersion will sometimes aggregate during the course of the purification procedure, dispersion treatment may be carried out by shearing or the like in such cases. The means used to apply shearing for the invention is a high-pressure homogenizer. Next, the physical properties of the obtained colored cellulose particles are measured.

[Preparation of Regenerated Cellulose Continuous Filament Nonwoven Fabric]

A stock solution obtained by dissolving cotton linter, having the foreign matter removed and having an adjusted polymerization degree, in a copper ammonium solution, is extruded from a spinning nozzle (spinneret) having a hole (stock solution discharge hole) and dropped into a funnel together with water for deammoniation to cause solidification of the stock solution, while stretching and loading it down onto a net to form a web. During this time, the oscillation in the direction perpendicular to the machine direction as the net proceeds produces a Sin curve in the fibers that are being loaded onto the net. Stretching during spinning may be to a factor of 100 to 500, and by changing the shape of the spinning funnel and the through-flow volume of spinning water it is possible to adjust the draw ratio as desired. By varying the draw ratio, it is possible to change the monofilament size or nonwoven fabric strength. For nonwoven fabric web formation, in order to obtain uniform fiber orientation, the fiber orientation as loaded onto the net is uniformly varied in 3 to 10 stages, with the phase of the Sin curve in layer units, to make a layered web of 3 to 10 layers, thereby allowing a cellulosic nonwoven fabric with a very uniform fiber orientation to be obtained. A multilayer structure nonwoven fabric having such uniform fiber orientation has uniform fiber gaps and a regular average pore size as a nonwoven fabric, and if the nonwoven fabric having such a uniform pore size is densified, it is possible to obtain a nonwoven fabric that is thin, dense and has uniform pore sizes. In addition, by varying the spinning water volume and temperature, it is possible to control the low molecular weight cellulose, or hemicellulose, remaining in trace amounts in the stock solution. Furthermore, by controlling the net traveling speed and oscillation width, it is possible to control the fiber orientation direction and to control the strength and ductility of the nonwoven fabric.

The shape of the spinning funnel is preferably rectangular, and preferably the length of the spinning funnel that directs downward flow is 100 to 400 mm and the slit width of the downflow outlet is 2 to 5 mm. The diameter of the stock solution discharge hole of the spinneret is preferably 0.1 to 0.5 mm, and the shape is preferably round. Also, in terms of ensuring homogeneity of the nonwoven fabric, the web is preferably layered to form a nonwoven fabric, the number of layers being preferably 3 to 10. For example, following the method described in Japanese Patent Publication No. 787914 or Japanese Patent Publication No. 877579, the layered web is scoured after regenerating the cellulose in the web form, and then the fibers are tangled with a high-pressure water jet to produce a nonwoven fabric. Holes or irregularities can be produced in the nonwoven fabric during this time to impart a design property, by the high-pressure water jet conditions and the form of the net situated below and/or above the nonwoven fabric. The obtained nonwoven fabric can be obtained as a dried and wound product. This is referred to as a continuous filament nonwoven fabric because a series of steps is carried out from spinning until winding so that the fibers are continuously connected without breakage. The physical properties of the obtained regenerated cellulose continuous filament nonwoven fabric are then measured.

[Method of Preparing Immunochromatographic Diagnostic Kit]

A dispersion of colored cellulose particles adjusted to a prescribed concentration is prepared, the buffering solution and antibody are added, and stirring is carried out for a prescribed time while adjusting the temperature, for adsorption of the antibody onto the colored cellulose particles. After stirring for the prescribed time, a blocking agent is further added and stirring is continued for a prescribed time while adjusting the temperature, for blocking of the colored cellulose particles. The blocking agent used may be any of various blocking agents depending on the substance to be examined or the specimen, or the composition of their diluted solution. The casein used for the invention is particularly preferred for blocking of the colored cellulose particles. For washing of the colored cellulose particles that have been subjected to antibody adsorption and blocking, centrifugal separation is carried out, the supernatant liquid containing excess antibody and blocking agent, and the precipitated particles, are separated and the supernatant liquid is removed by decantation. Liquids such as a buffering solution are added to the precipitated particles, and if necessary dispersion treatment is carried out using ultrasonic waves or the like. The washing by the series of procedures including precipitation by centrifugal separation, removal of the supernatant and addition of liquids, is carried cut the necessary number of times, and a dispersion is prepared containing a prescribed concentration of the particles that have been subjected to antibody adsorption and blocking. As necessary, proteins, surfactants or sugars such as sucrose or trehalose are added to the dispersion, and the obtained solution is coated in a prescribed amount onto a polyethylene conjugate pad and dried to prepare a detection reagent-containing section. Also, if necessary, the regenerated cellulose continuous filament nonwoven fabric my be coated with a buffering solution, a surfactant, a protein, a reagent that traps contaminants in the specimen sample, an antiseptic agent, an antimicrobial agent, an antioxidant, a humectant or the like, and dried to prepare the sample pad. In addition, there are prepared a nitrocellulose porous membrane-composed chromatographic medium immobilizing an antibody at a prescribed location, and a cellulose filter paper absorbent pad for absorption of the antibody. These are immobilized on a mount board having an attachment site called a backing sheet, and cut to a prescribed size to prepare the immunochromatographic diagnostic kit.

EXAMPLES

The present invention will now be explained in greater detail through the following examples, with the understanding that these examples are in no way limitative on the invention. All of the procedures that are not described in particular were conducted in an environment with a temperature of 23° C. and a relative humidity of 55%.

[Measurement of Average Particle Diameter of Chromogenic Particles]

The apparatus used was a Nanotrac UPA-EX150 particle size distribution analyzer (dynamic light scattering-type) by Nikkiso Co., Ltd. The measuring sample used was a sample comprising 0.01 wt % chromogenic particles and 99.99 wt % purified water. The measuring conditions were a number of scans of 30 and a measuring time of 30 seconds per measurement, and the volume-average particle size distribution was used, recording the median diameter as the average particle diameter. Also, the standard deviation of the particle size distribution and the average particle diameter obtained from the 30 scans were used to calculate the CV value.

[Measurement of Color Intensity of Chromogenic Particles]

The apparatus used was a JASCO V-650 ultraviolet/visible/near-infrared spectrophotometer by JASCO Corp. (optical system: single monochromator, Czerny-Turner mount, double-beam system, light source: deuterium lamp (190 to 350 nm), halogen lamp (330 to 900 nm)) with a mounted integrating sphere unit ISV-722 by the same manufacturer. The sample used for measurement was an aqueous dispersion of chromogenic particles at an arbitrary concentration, or dry particles, adjusted to a concentration of 0.01 wt % chromogenic particle and 99.99 wt % purified water using distilled water as the dispersing medium. The concentration-adjusted aqueous dispersion was added in an amount of 2.5 mL to a quartz cell with an optical path length of 10 mm (volume: 3.5 mL, optical path width: 10 mm), and the quartz cell was set in the sample holder of an ultraviolet/visible/near-infrared spectrophotometer, upon which measurement was carried out. Of the obtained absorbance peaks, the maximum (ABS) in the visible light range of 400 to 800 nm was recorded as the color intensity.

[Calculation of Proportion of Colorant in Chromogenic Particles]

This was calculated from the weight of chromogenic particles after the prescribed number of coloration procedures, and the weight of the particles before coloration. For example, when 1.0 g of cellulose particles were colored and 2.5 g of colored cellulose particles were obtained, the colorant was calculated as being 2.5 g–1.0 g–1.5 g. The proportion of colorant in this case is 1.5 g+2.5 g×100=60.0 wt %.

[Calculation of Proportion of Cellulose-Derived Component of Chromogenic Particles]

As explained above, the calculation was performed by the formula: "Proportion of cellulose-derived component of the chromogenic particles"=100%–(proportion of the colorant in the chromogenic particles).

[Measurement of L/D Ratio of Chromogenic Particles]

The apparatus used was a JSM-6700 scanning electron microscope by JEOL Corp. A sample with 0.01 wt % chromogenic particles and 99.99 wt % purified water was dropped onto a mica board, and after 10 seconds, the chromogenic particles became adsorbed onto the mica plate, the excess liquid was wiped off with a Kimwipe, and it was allowed to dry. The obtained mica plate was coated with platinum to prepare a sample for electron microscope measurement. This was observed at an acceleration voltage of 1.6 kV and a 50,000× measuring magnification, a number of images were taken as necessary for at least 100 particle images, and the long diameter (L) and short diameter (D) of each of the particles was measured and used to calculate the average value of L/D of 100 particles.

[Measurement of Nonwoven Fabric Thickness]

This was measured by the thickness test of JIS-L1096, with a load of 1.96 kPa (units: mm).

[Measurement of Nonwoven Fabric Basis Weight]

A nonwoven fabric with an area of at least 0.5 m$^2$ was dried at 105° C. to a fixed weight, and then allowed to stand for at least 16 hours in a thermostatic chamber at 20° C., 65% RH, the weight was measured, and the weight per unit area of the nonwoven fabric was measured (units: g/m$^2$).

[Measurement of Nonwoven Fabric Bulk Density]

This was calculated by dividing the weight per unit area of the nonwoven fabric by the thickness (units: g/cm$^3$).

[Measurement of Nonwoven Fabric Fiber Loss Number]

A 25 cm×25 cm sample was placed in 300 ml of purified water and allowed to stand for 2 minutes. The number of fibers lost that had sizes of 100 μm or greater were counted with a video microscope, after removing the sample and filtering the remaining fluid with black filter paper (AD-VANTEC NO131), setting the filter paper after filtration in a thermostatic chamber (20° C., 65% RH) for 12 hours and drying (units: number/m$^2$).

[Measurement of Diagnosis Time with Immunochromatographic Diagnostic Kit]

The immunochromatographic diagnostic kit cut to a 5 mm width was placed in a plastic housing. The thus obtained diagnostic kit in the housing was measured using a C10066-10 Immunochromato-Reader by Hamamatsu Photonics, K.K. The apparatus was set according to the color of the particles used. Human chorionic gonadotropin (hereunder, "hCG") was used as the substance to be examined, diluting the hCG with 66 mM phosphate buffer (hereunder, "PBS") at pH 7.4 containing 1 wt % bovine serum albumin (hereunder, "BSA"), to prepare a positive specimen with an hCG concentration of 10 mIU/ml, A 120 μl portion of the positive specimen was dropped into the sample dropping section of the diagnostic kit, and measurement was performed with the Immunochromato-Reader every 20 seconds thereafter, determining the change in the TL over time. The reason for measurement every 20 seconds is that just less than 20 seconds is necessary for each measurement. The time at which the color intensity of the TL obtained by the Immunochromato-Reader (units: mABS) was 20 mABS or greater was recorded. The reason for the index of 20 mABS is because the presence of a TL becomes visible at 20 mABS or greater, with variation depending on individual differences. The measurement was conducted 5 times, and the average time was recorded as the diagnosis time.

[Measurement of Reproducibility with Immunochromatographic Diagnostic Kit]

In the same manner as above, a 120 μl positive specimen was dropped onto the sample dropping section of the diagnostic kit, and after 15 minutes had elapsed, the TL color intensity was measured with an Immunochromato-Reader. The measurement was performed 20 times, the average value of the obtained values was recorded as the TL intensity, and the standard deviation was recorded as the standard deviation of TL intensity. The index % CV, indicating the reproducibility, was calculated by the following formula (1).

% CV=TL intensity standard deviation/TL intensity×100    [Formula (1)]

[Measurement of False Positivity with Immunochromatographic Diagnostic Kit]

A 66 mM PBS solution at pH 7.4 containing 1 wt % BSA was prepared as a negative specimen. A 120 μl negative specimen was dropped onto the sample dropping section of the diagnostic kit, and after 15 minutes had elapsed, the TL color intensity was measured with an Immunochromato-Reader. The measurement was performed 5 times, with lack of false positivity being defined as an average value of 5 mABS or lower. The reason for the index of 5 mABS is because the presence of a TL cannot be visually confirmed at 5 mABS or lower, with variation depending on individual differences.

[Measurement of Detection Limit with Immunochromatographic Diagnostic Kit]

Serially diluted positive specimens were prepared with hCG concentrations of 3.20 mIU/ml, 1.60 mIU/ml, 0.80 mIU/ml, 0.40 mIU/ml, 0.20 mIU/ml, 0.10 mIU/ml, 0.05 mIU/ml and 0.025 mIU/ml. In the same manner as above, 120 μl was dropped onto the sample dropping section of the diagnostic kit, and after 15 minutes had elapsed, the TL color intensity was measured with an Immunochromato-Reader. The measurement was performed 5 times at each concentration, and when the average value of the obtained values was at least 20 mABS above the value measured for the negative specimen a judgment of positivity was made, or when it was below, it was considered to be below the detection limit. The lower limit of the hCG concentration that gave a positive judgment was defined as the detection limit.

Example 1

[Preparation of Antibody-Sensitized Colored Cellulose Particles]

A 120 μl portion, of 1.0 wt % colored cellulose particles 1 (average particle diameter: 352 nm, color intensity: 2.9 ABS, colorant proportion: 49%), prepared by a known method, was placed in a 15 ml centrifuge tube, and then 240 μl of Tris-buffering solution (50 mM, pH 7.0) and 120 μl of 0.1% anti-hCG-α mouse antibody (10-C25C, product of Fitzgerald) were added and the mixture was stirred for 10 seconds with a vortex. It was then placed in a dryer adjusted to 37° C. and allowed to stand for 120 minutes. Next, 14.4 ml of blocking solution (100 mM boric acid, pH 8.5) containing 1.0 wt % casein (030-01505 by Wako Pure Chemical Industries, Ltd.) was added, and the mixture was further allowed to stand for 60 minutes in a dryer at 37° C. A centrifugal separator (6200 by Kubota Corp.) and a centrifugal separation rotor (AF-5008C by Kubota Corp.) were then used for centrifugation at 10,000 g for 15 minutes, and upon precipitation of the sensitized particles, the supernatant was removed off. Next, 14.4 ml of borate buffer (50 mM boric acid, pH 10.0) was added and treatment was performed for 10 seconds with an ultrasonic disperser (UH-50 by SMT Co.). Centrifugation was then performed at 10,000 g for 15 minutes, and upon precipitation of the sensitized particles the supernatant was removed off. After then adding 0.6 g of sucrose (196-00015 by Wako Pure Chemical Industries, Ltd.) and 0.8 g of a 1.0 wt % casein blocking solution, borate buffer (50 mM boric acid, pH 10.0) was used to adjust the weight to 4.0 g, and a 0.03 wt % antibody-sensitized colored cellulose particle dispersion was prepared and treated with the ultrasonic disperser for 10 seconds.

[Impregnation of Antibody-Sensitized Colored Cellulose Particles into Conjugate Pad and Drying]

A polyethylene conjugate pad (6613 by Pall Co.) was dipped in a large excess of 0.05 wt % Tween-20 (T2700 by Sigma-Aldrich Japan, KK.), and after removing off the excess liquid, it was dried at 50° C. for 60 minutes. It was then cut into a shape with a height of 10 mm and a length of 300 mm. Next, a micropipette was used for even coating of 1020 μl of the 0.03 wt % antibody-sensitized colored cellulose particle dispersion, after which the pad was dried at 50° C. for 60 minutes.

[Pretreatment of Regenerated Cellulose Continuous Filament Nonwoven Fabric Sample Pad]

A regenerated cellulose continuous filament nonwoven fabric 1 (basis weight: 57.2 g/m$^2$, thickness: 0.52 mm, bulk density: 0.11 g/cm$^3$, fiber loss numbers 2000), prepared by a known method, was impregnated with PBS buffering solution (66 mM, pH 7.4) containing a large excess of 2.0 wt % BSA (A7906 by Sigma-Aldrich Japan, KK.) and 2.0 wt % Tween-20, and after removing off the excess liquid, it was dried at 50° C. for 60 minutes. It was then cut into a shape with a height of 20 mm and a length of 300 mm.

[Preparation of Capture Antibody-Coated Nitrocellulose Membrane]

A nitrocellulose membrane (SHF0900425 by Millipore) was cut into a shape with a height of 25 mm and a length of 300 mm. A liquid coating applicator (300DS by Musashi Engineering, Inc.) was used for coating of a PBS solution (66 mM, pH 7.4) containing 0.1 wt % anti-hCG-β mouse antibody (6601 by MedixBiochemica) at a proportion of 0.1 μl/mm onto a 7 mm-high section. Next, a PBS solution (66 mM, pH 7.4) containing 0.1 wt % anti-mouse-rabbit antibody (Z0259 by Daco Co.) was coated at a proportion of 0.1 μl/mm onto a 12 mm-high section. It was then dried at 37° C. for 30 minutes.

[Preparation of Immunochromatographic Diagnostic Kit]

Onto a backing card (AR9020 by Adhesives Research) there were attached the prepared capture antibody-coated nitrocellulose membrane, an absorbent pad (C083 by Millipore), the antibody-sensitized colored cellulose particle-containing conjugate pad and the regenerated cellulose continuous filament nonwoven fabric sample pad, in the layout illustrated in FIG. 1. The layout was then cut to a 5 mm width with a cutter, to obtain an immunochromatographic diagnostic kit with a width of 5 mm and a height of 60 mm.

[Performance Evaluation of Immunochromatographic Diagnostic Kit]

The performance of the obtained immunochromatographic diagnostic kit was evaluated. The results are shown in Table 1 below.

Example 2

An immunochromatographic diagnostic kit was prepared by the same method as Example 1, except that the chromogenic particles were colored cellulose particles 2 (average particle diameter: 588 nm, color intensity: 2.7 ABS, colorant proportion: 45%), and the performance was evaluated. The results are shown in Table 1 below.

Example 3

An immunochromatographic diagnostic kit was prepared by the same method as Example 1, except that the chromogenic particles were colored cellulose particles 3 (average particle diameter: 790 nm, color intensity: 2.6 ABS, colorant proportion: 42%), and the performance was evaluated. The results are shown in Table 1 below.

Example 4

An immunochromatographic diagnostic kit was prepared by the same method as Example 1, except that the chromogenic particles were colored cellulose particles 4 (average particle diameter: 185 nm, color intensity: 3.4 ABS, colorant proportion: 61%), and the performance was evaluated. The results are shown in Table 1 below.

Example 5

An immunochromatographic diagnostic kit was prepared by the same method as Example 1, except that the chromogenic particles were colored cellulose particles 5 (average particle diameter: 394 nm, color intensity: 4.8 ABS, colorant proportion: 75%), and the performance was evaluated. The results are shown in Table 1 below.

Example 6

An immunochromatographic diagnostic kit was prepared by the same method as Example 1, except that the chromogenic particles were colored cellulose particles 6 (average particle diameter: 332 nm, color intensity: 1.5 ABS, colorant proportion: 32%), and the performance was evaluated. The results are shown in Table 1 below.

Example 7

An immunochromatographic diagnostic kit was prepared by the same method as Example 1, except that the nonwoven fabric used in the sample pad was a regenerated cellulose continuous filament nonwoven fabric 2 (basis weight: 72.0 g/m$^2$, thickness: 0.08 mm, bulk density: 0.90 g/cm$^3$, fiber loss number: 1100), and the performance was evaluated. The results are shown in Table 1 below.

Example 8

An immunochromatographic diagnostic kit was prepared by the same method as Example 1, except that the nonwoven fabric used in the sample pad was a regenerated cellulose continuous filament nonwoven fabric 3 (basis weight: 50.3 g/m$^2$, thickness: 0.75 mm, bulk density: 0.07 g/cm$^3$, fiber loss number: 2100), and the performance was evaluated. The results are shown in Table 1 below.

Example 9

An immunochromatographic diagnostic kit was prepared by the same method as Example 1, except that the nonwoven fabric used in the sample pad was a regenerated cellulose continuous filament nonwoven fabric 4 (basis weight: 17.9 g/m$^2$, thickness: 0.13 mm, bulk density: 0.14 g/cm$^3$, fiber loss number: 1500), and the performance was evaluated. The results are shown in Table 1 below.

Example 10

An immunochromatographic diagnostic kit was prepared by the same method as Example 1, except that the nonwoven fabric used in the sample pad was a composite nonwoven fabric (basis weight: 92.5 g/m$^2$, thickness: 0.30 mm, bulk density: 0.31 g/cm$^3$, fiber loss number: 900) obtained by hydroentangling a regenerated cellulose continuous filament nonwoven fabric (basis weight: 61.5 g/m$^2$) and a polyester nonwoven fabric (basis weight: 32.0 g/m$^2$) with a water jet, and the performance was evaluated. The results are shown in Table 1 below.

Example 11

An immunochromatographic diagnostic kit was prepared by the same method as Example 1, except that the Kinocloth method was employed as a method of forming a dry airlaid nonwoven fabric, in which cuprammonium fibers were cut to fiber lengths of 30 mm and dispersed in air together with a hydrophilic binder to form layering, and a regenerated cellulose staple fiber nonwoven fabric 1 (basis weight: 49.2 g/m$^2$, thickness: 0.24 mm, bulk density: 0.21 g/cm$^3$, fiber loss number: 10,500) thus prepared was used as the sample pad, and the performance was evaluated. The results are shown in Table 1 below.

Example 12

An immunochromatographic diagnostic kit was prepared by the same, method as Example 1, except that the fibers used were lyocell fibers, and a regenerated cellulose staple fiber nonwoven fabric 2 (basis weight: 61.3 g/m$^2$, thickness: 0.50 mm, bulk density: 0.12 g/cm$^3$, fiber loss number: 8900) was prepared by the same method as in Example 11 and used as the sample pad, and the performance was evaluated. The results are shown in Table 1 below.

Example 13

An immunochromatographic diagnostic kit was prepared by the same method as Example 1, except that the fibers used were rayon fibers, and a regenerated cellulose staple fiber nonwoven fabric 3 (basis weight: 31.7 g/m$^2$, thickness: 0.19 mm, bulk density: 0.17 g/cm$^3$, fiber loss number: 10,000) was prepared by the same method as in Example 11 and used as the sample pad, and the performance was evaluated. The results are shown in Table 1 below.

Explanation of Examples 1 to 13

In all of Examples 1 to 13, by using prescribed chromogenic particles with large particle diameters and high color intensity together with a sample pad that was a prescribed nonwoven fabric made of regenerated cellulosic fibers, having low bulk density and low thickness, it was possible to obtain an immunochromatographic diagnostic kit with rapid coloration, exhibiting line coloration within 1 minute, a short diagnosis time, high analysis sensitivity and excellent reproducibility of results, as shown in Table 1 below.

Comparative Example 1

An immunochromatographic diagnostic kit was prepared by the same method as Example 1, except that the chromogenic particles were colored cellulose particles 7 with small particle diameters (average particle diameter: 69 nm, color intensity: 2.8 ABS, colorant proportion: 48%), and the performance was evaluated. The results are shown in Table 1 below. As clearly seen by the results shown in Table 1, a small average particle diameter of the chromogenic particles resulted in line coloration after 1 minute, a slow diagnosis time and low analysis sensitivity.

Comparative Example 2

An immunochromatographic diagnostic kit was prepared by the same method as Example 1, except that, the chromogenic particles were colored cellulose particles 8 with large particle diameters (average particle diameter: 1017 nm, color intensity: 2.4 ABS, colorant proportion: 41%), and the performance was evaluated. The results are shown in Table 1 below. As clearly seen by the results shown in Table 1, a large average particle diameter of the chromogenic particles resulted in particle clogging, or some delay in diagnosis time, leading to poor reproducibility and also false positivity. The conjugate pad or nitrocellulose membrane was also colored.

Comparative Example 3

An immunochromatographic diagnostic kit was prepared by the same method as Example 1, except that the chromogenic particles were colored latex particles (average particle diameter: 351 nm, color intensity: 0.4 ABS, colorant proportion unknown), and the performance was evaluated. The results are shown in Table 1 below. As clearly seen by the results shown in Table 1, when the chromogenic particles were latex particles, the particle color intensity was low, the diagnosis time was slow and the analysis sensitivity was low.

Comparative Example 4

An immunochromatographic diagnostic kit was prepared by the same method as Example 1, except that the chromogenic particles were gold colloid (average particle diameter: 63 nm, color intensity: 2.3 ABS), and the performance was evaluated. The results are shown in Table 1 below. As clearly seen by the results in Table 1, when the chromogenic particles were gold colloid particles, the particle diameter was small, the diagnosis time was slow, the analysis sensitivity was low and the reproducibility of results was poor.

Explanation of Comparative Examples 1 to 4

As clearly seen by comparison between Examples 1 to 13 and Comparative Examples 1 to 4, when the particle diameters of the chromogenic particles were not within the optimal range or the color intensity was low, as in Comparative Examples 1 to 4, it was not possible to provide a diagnostic kit simultaneously exhibiting all of the desired properties for examination time, analysis sensitivity, reproducibility of results and presence or absence of false positivity.

Comparative Example 5

An immunochromatographic diagnostic kit was prepared by the same method as Example 1, except that the sample pad was a low-basis-weight regenerated cellulose continuous filament nonwoven fabric 5 (basis weight: 9.1 g/m$^2$, thickness: 0.12 mm, bulk density: 0.08 g/cm$^3$, fiber loss number: 2900), and the performance was evaluated. The results are shown in Table 1 below. When the basis weight of the nonwoven fabric made of regenerated cellulosic fibers used for the sample pad was low, some of the diagnostic kits had leakage of a portion of the specimen fluid from the top of the diagnostic kit, and sufficient liquid volume could not be supplied to the conjugate pad, resulting in poor release of the particles. Therefore, some of the diagnostic kits had slow diagnosis time, low analysis sensitivity and, consequently, poor reproducibility of results. In addition, at the stage of pretreatment of the sample pad, the wet handling was poor and management was difficult.

Comparative Example 6

An immunochromatographic diagnostic kit was prepared by the same method as Example 1, except that the sample pad was a regenerated cellulose continuous filament nonwoven fabric 6 having a high basis weight and a large thickness (basis weight: 170 g/m$^2$, thickness: 1.09 mm, bulk density: 0.16 g/cm$^3$, fiber loss number: 2900), and the performance was evaluated. The results are shown in Table 1 below. When the nonwoven fabric made of regenerated cellulosic fibers used in the sample pad had a high basis weight and a large thickness, release of the particles from the conjugate pad was poor, possibly because the sample pad itself retained some degree of liquid volume, while the diagnosis time was slow and the reproducibility of results was poor. The conjugate pad or nitrocellulose membrane was also colored.

Comparative Example 7

An immunochromatographic diagnostic kit was prepared by the same method as Example 1, except that the sample pad was a small-thickness regenerated cellulose continuous filament nonwoven fabric 7 (basis weight: 57.2 g/m$^2$, thickness: 0.05 mm, bulk density: 1.14 g/cm$^3$, fiber loss number: 1000), and the performance was evaluated. The results are shown in Table 1 below. When the nonwoven fabric made of regenerated cellulosic fibers used in the sample pad had a small thickness, release of the particles from the conjugate pad was poor, possibly because the bulk density was high, the liquid absorption speed was poor and the flow rate per unit time was not sufficient, while the diagnosis time was also slow and the reproducibility of results was poor. The conjugate pad or nitrocellulose membrane was also colored.

Comparative Example 8

An immunochromatographic diagnostic kit was prepared by the same method as Example 1, except that the sample pad was a pulp staple fiber nonwoven fabric 1 (basis weight: 68.0 g/m$^2$, thickness: 0.16 mm, bulk density: 0.43 g/cm$^3$, fiber loss number: 9200), and the performance was evaluated. The results are shown in Table 1 below. When a pulp staple fiber nonwoven fabric was used in the sample pad, release of the particles from the conjugate pad was poor, possibly because the hydrophilicity of the fibers themselves was low and the flow rate per unit time was not sufficient, while the diagnosis time was also slow and the reproducibility of results was poor. The conjugate pad or nitrocellulose membrane was also colored.

Comparative Example 9

An immunochromatographic diagnostic kit was prepared by the same method as Example 1, except that the sample pad was a pulp staple fiber nonwoven fabric 2 (commercially available immunochromatography sample pad, basis weight: 179.0 g/m$^2$, thickness: 0.48 mm, bulk density: 0.37 g/cm$^3$, fiber loss number: 11,100), and the performance was evaluated. The results are shown in Table 1 below. When a pulp staple fiber nonwoven fabric was used in the sample pad, release of the particles from the conjugate pad was poor, possibly because the hydrophilicity of the fibers themselves was low and the flow rate per unit time was not sufficient, while the diagnosis time was also slow and the reproducibility of results was poor. The conjugate pad or nitrocellulose membrane was also colored.

Explanation of Comparative Examples 5 to 9

As is clear by comparison between Examples 3 to 13 and Comparative Examples 5 to 9, when the basis weight and thickness of the nonwoven fabric made of regenerated cellulosic fibers used in the sample pad were made of fibers other than regenerated cellulosic fibers, as shown in Table 1, it was not possible to provide a diagnostic kit exhibiting all of the desired properties for diagnosis time, analysis sensitivity, reproducibility of results and presence or absence of false positivity.

Comparative Example 10

An immunochromatographic diagnostic kit was prepared by the same method as Example 1, except that the chromogenic particles were the gold colloid used in Comparative Example 4 and the sample pad was the pulp staple fiber nonwoven fabric 2 used in Comparative Example 9, and the performance was evaluated. The results are shown in Table 1 below. With this combination, the diagnosis time was very slow, the analysis sensitivity was low, and the reproducibility of results was poor.

Comparative Example 11

An immunochromatographic diagnostic kit was prepared by the same method as Example 1, except that the chromogenic particles were the colored latex particles used in Comparative Example 3 and the sample pad was the pulp staple fiber nonwoven fabric 2 used in Comparative Example 9, and the performance was evaluated. The results are shown in Table 1 below. With this combination, the diagnosis time was very slow, the analysis sensitivity was low, and the reproducibility of results was poor.

Comparison of Changes in TL Over Time in
Example 1, Comparative Example 4, Comparative
Example 9 and Comparative Example 10

Figure 5:
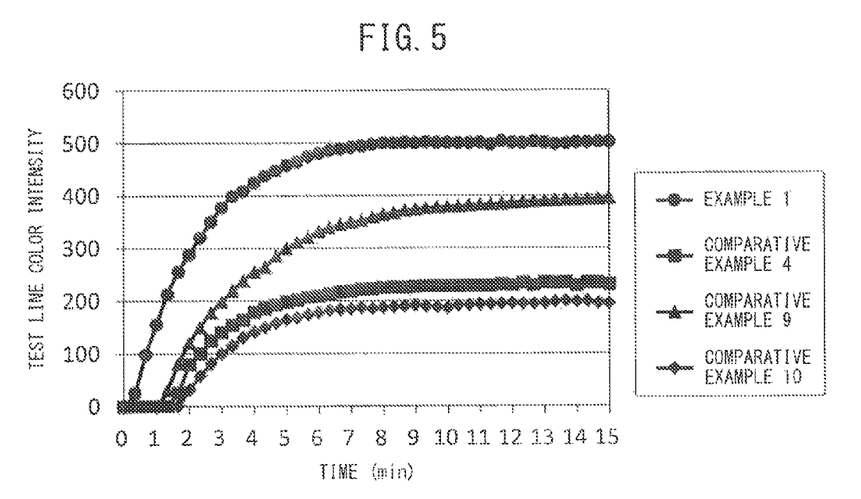
FIG. 5 is a graph showing the relationship between signal strength of examination results (TL color intensity) for examination of a positive specimen with constant concentration using an immunochromatographic diagnostic kit of the invention, and its change over time (min).

Using the results of measurement of the diagnosis time with the immunochromatographic diagnostic kits conducted in Example 1, Comparative Example 4, Comparative Example 9 and Comparative Example 10, comparison was made between the changes in TL color intensity over time. The results are shown in FIG. 5. As clearly seen from FIG. 5, Comparative Example 4 and Comparative Example 10 which used gold colloid for the chromogenic particles were largely unaffected by the sample pad. Also, Comparative Example 9 which used a commercial product immunochromatography sample pad for the sample pad, though using specific chromogenic particles, had moderately increased color intensity even after some time had elapsed. This is because the liquid absorption speed of the sample pad was not sufficient and the flow rate of the specimen fluid per unit time was slow, and therefore the chromogenic particles continued to be released from the conjugate pad. In contrast, the color intensity was very high in Example 1, and the color intensity rapidly stabilized. This is an effect of the combination of the prescribed chromogenic particles and the prescribed sample pad according to the invention, which supports the conclusion that the particles were released from the conjugate pad at an earlier stage.

When performance evaluation was conducted under exactly the same conditions as Example 1, Comparative Example 4 and Comparative Example 9, except that the hCG system was changed to an influenza system, the same effect was confirmed in the influenza system as in the hCG system.

Effect of Coverage Factor of Sample Pad on Conjugate Pad

Example 14

An immunochromatographic diagnostic kit was prepared by the same method as Example 1, except that the coverage factor of the sample pad on the conjugate pad was changed to 70% by using a sample pad length of 17 mm, and the performance was evaluated. The results are shown in Table 2 below.

Example 15

An immunochromatographic diagnostic kit was prepared by the same method as Example 1, except that the coverage factor of the sample pad on the conjugate pad was changed to 50% by using a sample pad length of 15 mm, and the performance was evaluated. The results are shown in Table 2 below.

Comparative Example 12

An immunochromatographic diagnostic kit was prepared by the same method as Example 1, except that the coverage factor of the sample pad on the conjugate pad was changed to 20% by using a sample pad length of 12 mm, and the performance was evaluated. The results are shown in Table 2 below.

As clearly seen by the results in Table 2, changing the coverage factor of the sample pad on the conjugate pad did not change the coloration time, but sometimes impaired the reproducibility of results.

TABLE 1

| | Chromogenic particles | | | Sample pad | |
|---|---|---|---|---|---|
| | Type | Average particle diameter (nm) | Color intensity (ABS) | Type | Basis weight (g/m$^2$) |
| Example 1 | Colored cellulose particles 1 | 352 | 2.9 | Regenerated cellulose continuous filament nonwoven fabric 1 | 57.2 |
| Example 2 | Colored cellulose particles 2 | 588 | 2.7 | Regenerated cellulose continuous filament nonwoven fabric 1 | 57.2 |
| Example 3 | Colored cellulose particles 3 | 790 | 2.6 | Regenerated cellulose continuous filament nonwoven fabric 1 | 57.2 |
| Example 4 | Colored cellulose particles 4 | 185 | 3.4 | Regenerated cellulose continuous filament nonwoven fabric 1 | 57.2 |
| Example 5 | Colored cellulose particles 5 | 394 | 4.8 | Regenerated cellulose continuous filament nonwoven fabric 1 | 57.2 |
| Example 6 | Colored cellulose particles 6 | 332 | 1.5 | Regenerated cellulose continuous filament nonwoven fabric 1 | 57.2 |
| Example 7 | Colored cellulose particles 1 | 352 | 2.9 | Regenerated cellulose continuous filament nonwoven fabric 2 | 72.0 |
| Example 8 | Colored cellulose particles 1 | 352 | 2.8 | Regenerated cellulose continuous filament nonwoven fabric 3 | 50.3 |
| Example 9 | Colored cellulose particles 1 | 352 | 2.9 | Regenerated cellulose continuous filament nonwoven fabric 4 | 17.9 |
| Example 10 | Colored cellulose particles 1 | 352 | 2.9 | Regenerated cellulose continuous filament/ester | 92.5 |
| Example 11 | Colored cellulose particles 1 | 352 | 2.9 | Regenerated cellulose staple fiber nonwoven fabric 1 | 45.2 |
| Example 12 | Colored cellulose particles 1 | 352 | 2.9 | Regenerated cellulose staple fiber nonwoven fabric 2 | 61.3 |
| Example 13 | Colored cellulose particles 1 | 352 | 2.9 | Regenerated cellulose staple fiber nonwoven fabric 3 | 31.7 |
| Comp. Ex. 1 | Colored cellulose particles 7 | 69 | 2.8 | Regenerated cellulose continuous filament nonwoven fabric 1 | 57.2 |
| Comp. Ex. 2 | Colored cellulose particles 8 | 1017 | 2.4 | Regenerated cellulose continuous filament nonwoven fabric 1 | 57.2 |
| Comp. Ex. 3 | Colored latex particles | 351 | 0.4 | Regenerated cellulose continuous filament nonwoven fabric 1 | 57.2 |
| Comp. Ex. 4 | Gold colloid | 63 | 2.3 | Regenerated cellulose continuous filament nonwoven fabric 1 | 57.2 |
| Comp. Ex. 5 | Colored cellulose particles 1 | 352 | 2.9 | Regenerated cellulose continuous filament nonwoven fabric 5 | 9.1 |
| Comp. Ex. 6 | Colored cellulose particles 1 | 352 | 2.9 | Regenerated cellulose continuous filament nonwoven fabric 6 | 170.0 |
| Comp. Ex. 7 | Colored cellulose particles 1 | 352 | 2.9 | Regenerated cellulose continuous filament nonwoven fabric 7 | 57.2 |
| Comp. Ex. 8 | Colored cellulose particles 1 | 352 | 2.9 | Pulp staple fiber nonwoven fabric 1 | 68.0 |
| Comp. Ex. 9 | Colored cellulose particles 1 | 352 | 2.9 | Pulp staple fiber nonwoven fabric 2 | 179.0 |
| Comp. Ex. 10 | Gold colloid | 63 | 2.3 | Pulp staple fiber nonwoven fabric 2 | 179.0 |

TABLE 1-continued

| | | | | | | | | | | |
|---|---|---|---|---|---|---|---|---|---|---|
| Comp. Ex. 11 | Colored latex particles | | 351 | | 0.4 | Pulp staple fiber nonwoven fabric 2 | | | 179.0 | |

| | Sample pad | | | Immunochromatography results | | | | | |
|---|---|---|---|---|---|---|---|---|---|
| | Thickness (mm) | Bulk density (g/cm$^3$) | Fiber loss number (1000) | Coloration time (sec) | TL intensity (mABS) | TL intensity S.D. (mABS) | % CV (%) | Detection limit (mIU/ml) | False positivity |
| Example 1 | 0.52 | 0.11 | 2.0 | 20 | 502 | 6.8 | 1.4 | 0.050 | No |
| Example 2 | 0.52 | 0.11 | 2.0 | 24 | 621 | 10.9 | 1.8 | 0.025 | No |
| Example 3 | 0.52 | 0.11 | 2.0 | 32 | 641 | 13.6 | 2.1 | 0.025 | No |
| Example 4 | 0.52 | 0.11 | 2.0 | 28 | 387 | 5.8 | 1.5 | 0.100 | No |
| Example 5 | 0.52 | 0.11 | 2.0 | 20 | 598 | 9.5 | 1.6 | 0.025 | No |
| Example 6 | 0.52 | 0.11 | 2.0 | 28 | 389 | 4.5 | 1.2 | 0.100 | No |
| Example 7 | 0.08 | 0.90 | 1.1 | 20 | 495 | 7.9 | 1.6 | 0.050 | No |
| Example 8 | 0.75 | 0.07 | 2.1 | 20 | 513 | 8.3 | 1.6 | 0.050 | No |
| Example 9 | 0.13 | 0.14 | 1.5 | 20 | 525 | 6.6 | 1.3 | 0.050 | No |
| Example 10 | 0.30 | 0.31 | 0.9 | 28 | 500 | 9.1 | 1.8 | 0.050 | No |
| Example 11 | 0.24 | 0.21 | 10.5 | 36 | 475 | 6.6 | 1.4 | 0.050 | No |
| Example 12 | 0.50 | 0.12 | 8.9 | 36 | 465 | 7.1 | 1.5 | 0.050 | No |
| Example 13 | 0.19 | 0.17 | 10.0 | 40 | 430 | 6.8 | 1.6 | 0.050 | No |
| Comp. Ex. 1 | 0.52 | 0.11 | 2.0 | 80 | 210 | 3.9 | 1.9 | 0.800 | No |
| Comp. Ex. 2 | 0.52 | 0.11 | 2.0 | 56 | 531 | 52.0 | 9.8 | 0.050 | Yes |
| Comp. Ex. 3 | 0.52 | 0.11 | 2.0 | 120 | 135 | 2.1 | 1.6 | 1.600 | No |
| Comp. Ex. 4 | 0.52 | 0.11 | 2.0 | 104 | 231 | 21.0 | 9.1 | 0.800 | No |
| Comp. Ex. 5 | 0.12 | 0.08 | 2.9 | 32 | 512 | 14.5 | 2.8 | 0.050 | No |
| Comp. Ex. 6 | 1.09 | 0.16 | 2.9 | 68 | 399 | 15.5 | 3.9 | 0.100 | No |
| Comp. Ex. 7 | 0.05 | 1.14 | 1.0 | 72 | 315 | 13.0 | 4.1 | 0.100 | No |
| Comp. Ex. 8 | 0.16 | 0.43 | 9.2 | 72 | 412 | 12.9 | 3.1 | 0.100 | No |
| Comp. Ex. 9 | 0.48 | 0.37 | 11.1 | 84 | 395 | 13.5 | 3.4 | 0.100 | No |
| Comp. Ex. 10 | 0.48 | 0.37 | 11.1 | 124 | 195 | 19.0 | 9.7 | 0.100 | No |
| Comp. Ex. 11 | 0.48 | 0.31 | 11.1 | 142 | 165 | 17.0 | 10.3 | 1.600 | No |

TABLE 2

| | Sample pad | | | | Immunochromatography results | | | |
|---|---|---|---|---|---|---|---|---|
| | Chromogenic particles Type | Type | Length (mm) | Coverage factor on conjugate pad (%) | Coloration time (sec) | TL intensity (mABS) | TL intensity S.D. (mABS) | % CV (%) |
| Example 1 | Colored cellulose particles 1 | Regenerated cellulose continuous filament nonwoven fabric 1 | 20 | 100% | 20 | 502 | 6.8 | 1.4 |
| Example 14 | Colored cellulose particles 1 | Regenerated cellulose continuous filament nonwoven fabric 1 | 17 | 70% | 20 | 498 | 7.5 | 1.5 |
| Example 15 | Colored cellulose particles 1 | Regenerated cellulose continuous filament nonwoven fabric 1 | 15 | 50% | 20 | 481 | 8.0 | 1.7 |
| Comp. Ex. 12 | Colored cellulose particles 1 | Regenerated cellulose continuous filament nonwoven fabric 1 | 12 | 20% | 20 | 459 | 12.0 | 2.6 |

INDUSTRIAL APPLICABILITY

The immunochromatographic diagnostic kit of the invention allows rapid diagnosis, has high analysis sensitivity, and also excellent reproducibility of examination results, and can therefore be suitably used as a diagnostic reagent.

EXPLANATION OF SYMBOLS (a) Sample pad
(b) Conjugate pad containing antibody-sensitized chromogenic particles
(c) Detector A (TL)
(d) Detector B (control line)
(e) Chromatographic medium
(f) Absorbent pad
(g) Mount board
(h) Furthest downstream section of sample pad, with a coverage factor of the sample pad on the conjugate pad of 100%.
(i) Furthest downstream section of sample pad, with a coverage factor of the sample pad on the conjugate pad of 50%.
(j) Enclosure

What is claimed is:

1. An immunochromatographic diagnostic kit comprising:
 a conjugate pad containing a conjugate that includes chromogenic particles bound to an antibody that binds to a substance to be detected, the particles having an average particle diameter of 100 to 1000 nm and a color intensity of 1.0 to 10.0, the particle weight being 10 to 90 wt % derived from cellulose and 90 to 10 wt % derived from a colorant, a sample pad for first receiving the substance to be detected, the sample pad being in the form of a nonwoven fabric made of regenerated cellulosic fibers, with a basis weight of 10 to 150 g/m² and a thickness of 0.07 to 1.00 mm, a chromatographic medium, which is a nitrocellulose membrane with a flow rate of faster than 120 sec/4 cm, and on which an antibody that binds to the substance to be detected is immobilized, wherein the coverage factor of the sample pad on the conjugate pad, which is the proportion of coverage by the sample pad with respect to the top area of the conjugate pad is 70 to 100%, and wherein the sample pad, the conjugate pad and the chromatographic medium are arranged laterally in order while the conjugate pad covers a part of the top area of the chromatographic medium.

2. An immunochromatographic diagnostic kit according to claim 1, wherein the regenerated cellulosic fibers consist essentially of cuprammonium rayon fibers.

3. An immunochromatographic diagnostic kit according to claim 1 or 2, wherein the regenerated cellulosic fibers are continuous filaments.

4. An immunochromatographic diagnostic kit according to claim 1 or 2, wherein the fiber loss number of the nonwoven fabric made of regenerated cellulosic fibers is less than 5000/m2.

5. An immunochromatographic diagnostic kit according to claim 1 or claim 2, wherein the colorant is a reactive dye.

* * * * *